United States Patent [19]

Miles

[11] Patent Number: 5,291,336
[45] Date of Patent: Mar. 1, 1994

[54] MICROBEAM HOLDER

[76] Inventor: Gregory M Miles, 1925 McKinley Ave., Ste. D, La Verna, Calif. 91750

[21] Appl. No.: 724,784

[22] Filed: Jul. 2, 1991

[51] Int. Cl.$^5$ .................. G02B 7/02; G02B 7/182; A61B 17/36
[52] U.S. Cl. .................. 359/808; 359/819; 359/871; 359/875; 606/18; 606/2
[58] Field of Search ........ 359/368, 379, 821, 822–830, 359/383–389, 808–812, 815–819, 871–876, 879–882; 351/221; 128/395, 6–13, 362; 606/4, 1, 10–19; 219/121.6, 121.78, 121.83

[56] References Cited

U.S. PATENT DOCUMENTS

| | | | |
|---|---|---|---|
| 4,141,362 | 2/1979 | Wurster | 606/14 |
| 4,228,341 | 10/1980 | Zandberg | 219/121.83 |
| 4,494,540 | 1/1985 | Erb | 128/6 |
| 4,528,983 | 7/1985 | Erb | 606/18 |
| 4,607,919 | 8/1986 | Gartner et al. | 359/368 |
| 4,976,528 | 11/1990 | Cuda | 359/875 |
| 5,054,896 | 10/1991 | Margolis | 359/823 |

*Primary Examiner*—Bruce Y. Arnold
*Assistant Examiner*—Thong Nguyen
*Attorney, Agent, or Firm*—Dennis W. Beech

[57] ABSTRACT

An improved microbeam holder to focus and control a laser beam to direct it to a target for laser beam microsurgery. The holder has a simple specular mirror holder and joystick mechanism for ease in laser beam direction. The laser beam holder allows focusing the laser beam during surgery. An attachment is included to hold the microbeam holder on the microscope apparatus being used for surgery and allows the microbeam holder to be rotated relative to the microscope. An adjustable hand rest is provided to allow ease in control of the joystick mechanism for laser beam direction.

4 Claims, 3 Drawing Sheets

MICROBEAM HOLDER

1. FIELD OF THE INVENTION

The present invention relates to an improved laser micro surgery directional control device including a joystick and holding mechanism for specular mirrors, an improved laser holding device and lens focusing system, and an improved microscope attachment ring and lens holder.

2. DESCRIPTION OF RELATED ART

Various types of devices currently exist for attaching equipment to microscopes and other operating room devices for ease of doctors use in performing operations. In the area of microsurgery using lasers, various holders exist and are patented, for example, U.S. Pat. Nos. 3,710,798; 4,406,525; 4,494,540.

In these existing inventions there is not a convenient method for focusing the laser beam during the doctor's performance of the operation. Although lasers can be mounted on the device, there are not easily usable lens focusing techniques. Some of the existing devices have joysticks and specular mirror systems which allow control of the laser beam relative to the target.

The instant device provides a simpler and more compact method of specular mirror and joystick control function. The size of the device allows the device to be moved much nearer to the patient. The mirror holder is mounted in a slot and allows mirror adjustment without complicated springs and bearings. The associated joystick tension is simply controlled by an integral collar with ball and spring combination. The lens and microscope attachment ring avoids the use of complicated pistons and other devices to provide attachment and ease of rotation of the connected device.

The laser mounting and lens focusing system uses fixed and variable lens elements to provide the ability to adjust the laser focus quickly as it is being used in the operating room. A simple groove and retaining ring arrangement allows for ease of refocusing the laser from cutting to cauterizing.

SUMMARY OF THE INVENTION

A primary objective of the present invention is to provide a simple and convenient method for adjusting the specular mirror used in microsurgery. Another object of the invention is to provide a convenient method to mount the laser and then easily focus it for use in microsurgery. A further object of the invention is to provide a simple but flexible method to mount the microsurgery mechanism to optical devices such as microscopes. Another object is to provide a simple adjustable position hand rest. In accordance with the description present herein other objects of this invention will become apparent when the description and drawings are reviewed.

DESCRIPTION OF THE PREFERRED EMBODIMENT

Figure 1:
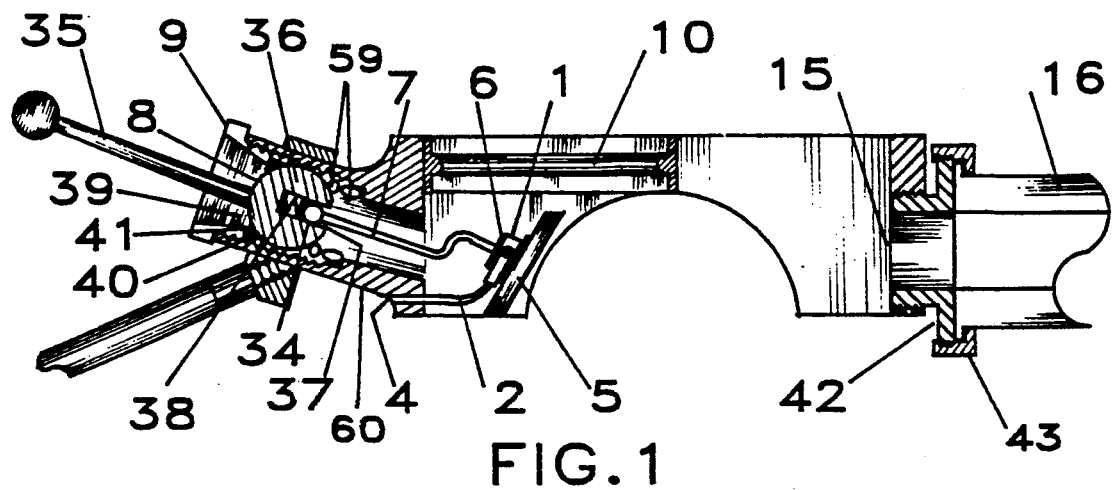
FIG. 1 illustrates a cut away view of a microbeam holder with the specular mirror and joystick.
Figure 2:
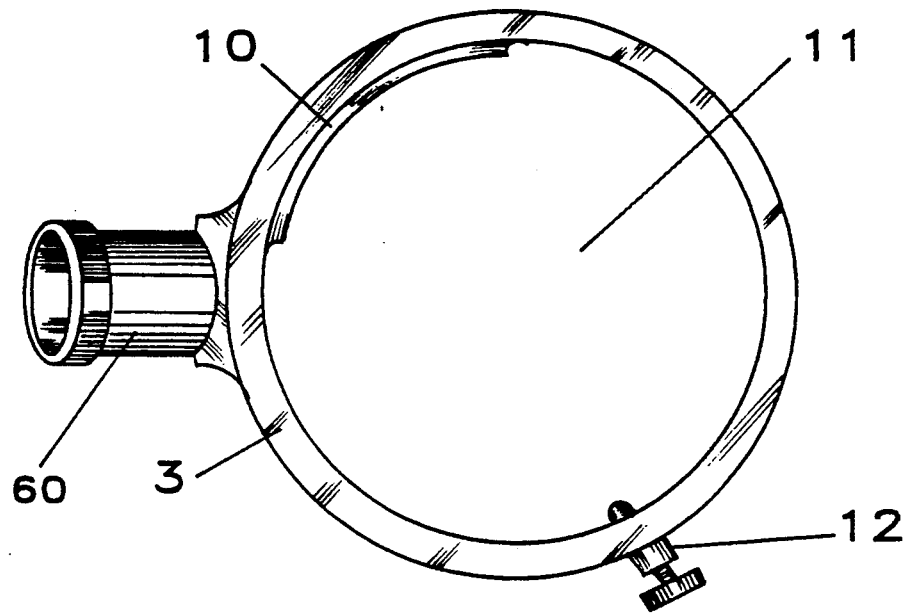
FIG. 2 illustrates a top view of the microbeam holder without joystick.
Figures 3, 4:
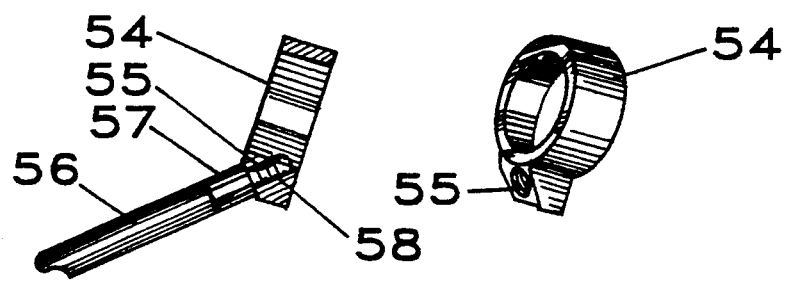
FIG. 3 illustrates a cut away view of the hand rest mechanism.
FIG. 4 illustrates a perspective view of the hand rest ring.
Figure 5:
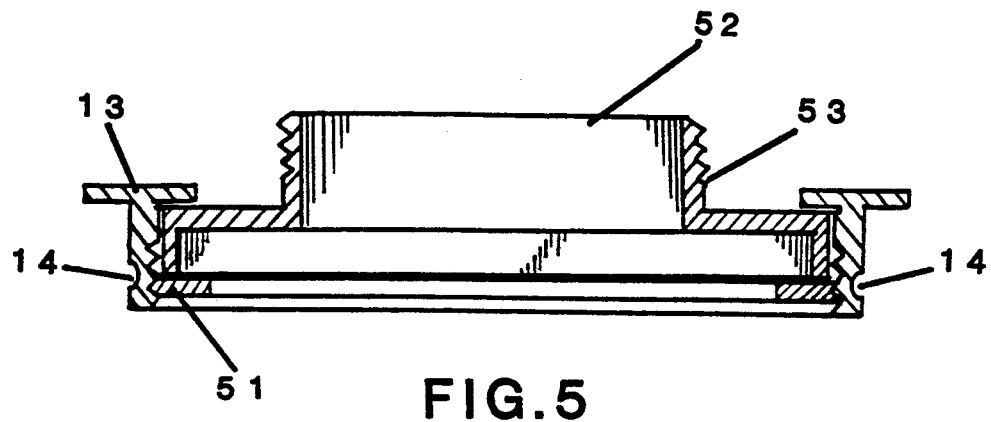
FIG. 5 illustrates a cut away view of the microscope attachment ring and lens holder.
Figure 1A:
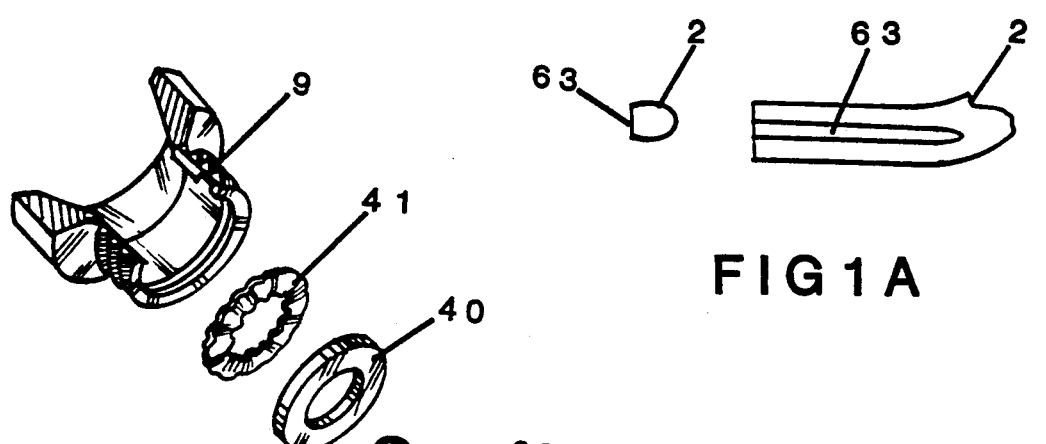
FIG. 1A illustrates the flat surface on the slip ring support.
Figure 6:
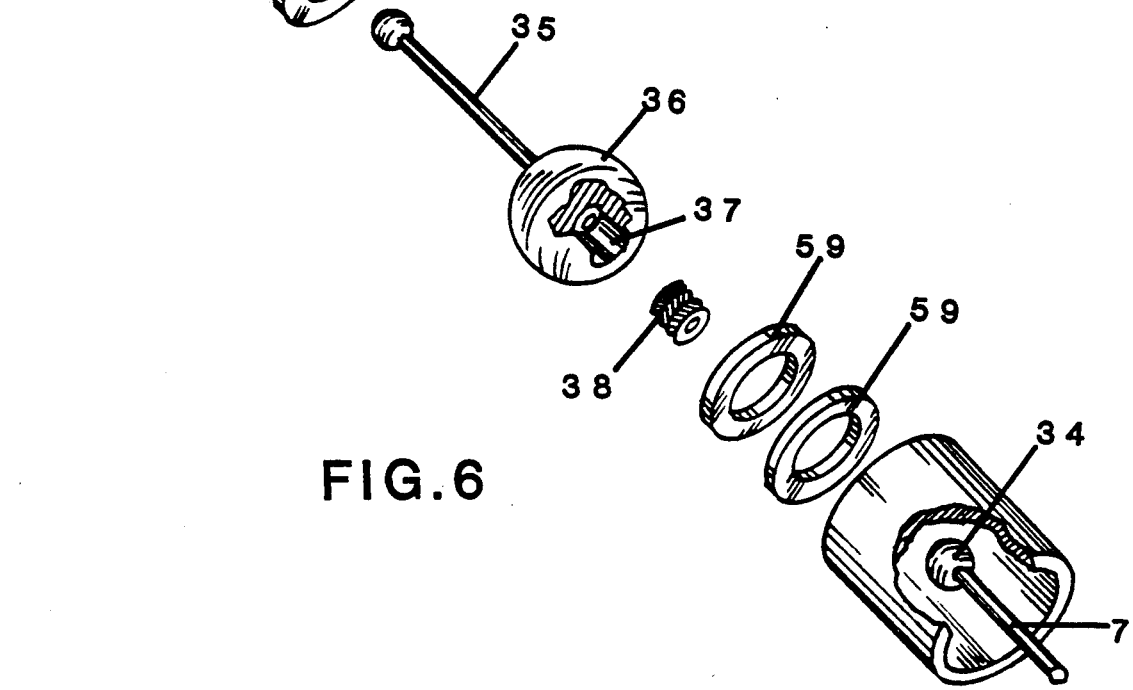
FIG. 6 illustrates a cut away perspective view of the joystick mechanism.

The microbeam holder is an annular device which has a laser and lens focusing device attached in a manner to allow the light beam to be reflected off a specular mirror and directed toward a target for surgery. The holder includes a joystick for control of the specular mirror to apply the laser to the point of interest. The holder also has a means for attachment of a microscope which includes a microscope attachment ring and lens holder to allow direct use of microscopes during an operation. The joystick mechanism has an adjustable hand rest associated with it.

Referring to FIGS. 1 through 6, a microbeam holder which consists of an annular housing (3) that has a slip ring (1) joined to a slip ring support (2) which is mounted to the microbeam holder by means of a support aperture (4) whose length determines the angular position relative to a target of two degrees to four degrees for the specular mirror (5). The slip ring support (2) has a flat surface (63) which mates with a flat plane in the support aperture (4) to orient the slip ring support (2). A set screw may be used to allow repositioning of the slip ring support (2). The specular mirror (5) is mounted to a mirror mount (6) to allow ease of replacement of the specular mirror (5). The mirror mount (6) is held in angular position by the slip ring (1) which allows the mirror mount (6) to rotate freely and is attached to an angled rod (7) which has a ball (34) at its end opposite the mirror mount (6).

A joystick mechanism (8) has a joystick handle (35) attached to a joystick ball (36) where the joystick ball (36) has a cylindrical aperture (37) therein of sufficient diameter to receive the ball (34). The cylindrical aperture (37) has a spring (38) mounted therein to put pressure on the ball (34) when the ball (34) is in the cylindrical aperture (37).

The joystick ball (36) is held in the joystick aperture (39) by the joystick retainer (9). The joystick retainer (9) has a retaining ring (40) and retaining ring washer spring (41) to provide tension control of the joystick mechanism (8) and rigidness of placement of the specular mirror (5). The joystick ball (36) is allowed to move freely or to be held firmly by twisting the joystick retainer (9) thus changing the pressure on the joystick ball (36). For ease of movement and tightening, there are two O-rings (59) opposite the retaining ring, (40) in the joystick aperature (39).

The joystick housing (60) portion of the annular housing (3) has a hand rest ring (54) with a hand rest (56) for resting the hand while manipulating the joystick handle (35). The hand rest ring (54) can rotate about the joystick housing (60) for proper positioning and then held firmly by turning the hand rest (56) by twisting it at the hand rest knurl (57) which locks the threaded hand rest lock (58) against the joystick housing (60) by means of the threaded hand rest aperature (55).

The microbeam holder has a protrusion (10) on the inside of the microscope viewing aperture (11) opposite a retaining key (12). The protrusion (10) and key (12) provide a means for attachment to a microscope to securely hold and allow rotation of a microscope and lens holder attachment ring (13). The retaining key (12) has a set screw retainer or similar device to prevent the retaining key (12) from being rotated outward too far and allowing the microbeam holder to come off the microscope. The attachment ring (13) has an annular groove (14) around its outside perimeter so located as to be retained by the protrusion (10) and key (12). The attachment ring (13) has a lens ring retainer (51) which retains lens (52) attached to a microscope for purposes of viewing the operation being performed. The lens ring retainer (51) is threaded into the attachment ring (13). The attachment ring (13) allows for compact distance between the microscope being used and the microbeam holder. The lens ring retainer (51) allows any reasonable diameter lens to be used for adaption to a microscope without concern for lens (52) thread size to be fitted into the attachment ring (13). The lens (52) has threads (53) to fit the microscope to which it normally attaches.

Figure 7:
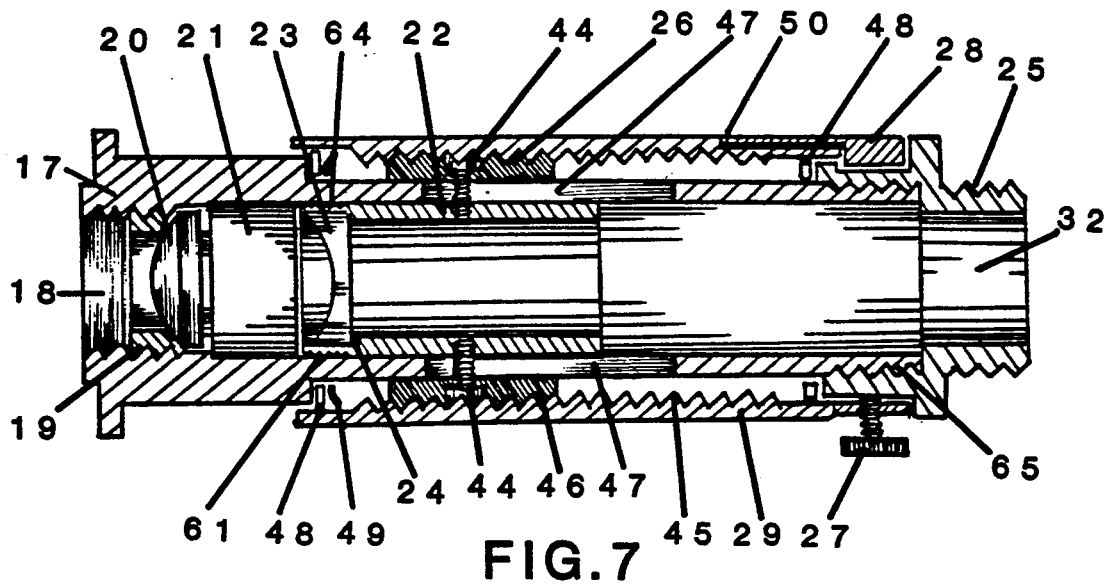
FIG. 7 illustrates a cut away view of the laser holder and lens focusing system.
Figure 8:
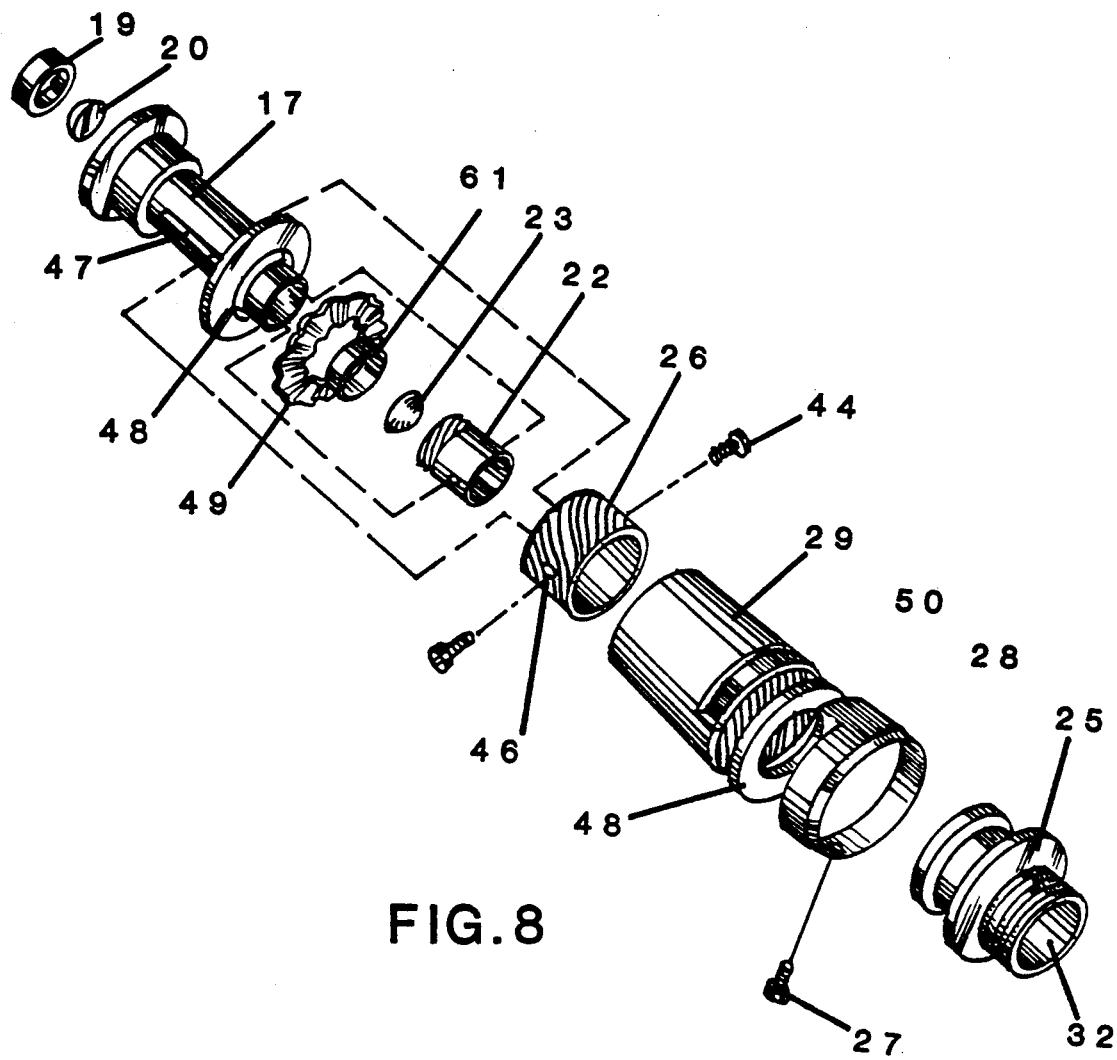
FIG. 8 illustrates a cut away perspective view of the laser holder and lens focus system.

Referring to FIGS. 1, 7 and 8 the microbeam holder has a laser holder mounting aperture (15) and laser holder retainer (42) for mounting a laser holder (16). The laser holder (16) has a positive lens mount (17) which defines a positive lens aperture (18) in which a positive lens retaining ring (19) is used to hold a positive lens (20). For this disclosure the use of positive lens and negative lens alone or as modifiers relates to the curvature or focusing of the lens such that the positive lens is convex on an outer surface or thicker at the middle and a negative lens is concave on an outer surface or thinner at the middle. The use of the term mount when associated with the lenses refers to the cylinder in when the appropriate lens is mounted to accomplish the focusing of the laser beam. The positive lens mount (17) is installed on the microbeam holder at the laser holder retainer (42) by means of the threaded laser holder ring (43).

The positive lens mount (17) defines a negative lens aperture (21) opposite the positive lens aperture (18) in which the negative lens mount (22) slides. The negative lens mount (22) is a hollow cylinder smooth on the outside. At one end of the negative lens mount (22) a negative lens (23) is mounted and held in place by a negative lens retaining groove (24) and a negative lens retainer (61) which threads over the negative lens threads (64) of negative lens mount (22). At the end opposite the positive lens (20) a laser mount (25) is attached to the positive lens mount (17) at the laser mount end (65). The laser mount (25) allows attachment of a laser device and defines a laser aperture (32) through which beam may pass to the negative lens (23).

The negative lens mount (22) slides into the positive lens mount (17) and is retained by a negative lens mount retaining ring (26). The negative lens mount retaining ring (26) and negative lens mount (22) are attached by screws (44). When the focus ring (29) is turned, the negative lens mount retaining ring (26) is moved by the focus threads (45) of the focus ring (29) and the retaining ring threads (46) axially along the positive lens mounts (17). The screws (44) are allowed to move via the slotted apertures (47) in the walls of the positive lens mount (17).

The negative lens mount retaining ring (26) is stopped or prevented from further axial travel by the washer (48) and lens wave washer ring (49) at the positive lens end of the positive lens mount (17) and by the washer (48) at the laser mount (25) at the opposite end. The washers (48) provide support for the focus ring (29) such that when rotated, metal does not rub on metal.

The spot size retaining ring (28) and retaining screw (27) allow only 180 degrees of turn on the focus ring (29) when the retaining screw (27) is tightened against the laser mount (25). The 180 degrees of freedom turn is defined by the turn groove (50) in the focus ring (29). This allows the laser beam to be spot sized at different microscope focal lengths. With a selected focal length, the smallest spot size is selected with the focus ring (29) and retaining screw (27) is tightened. This prevents focusing the laser in the body. The focus ring can have markings to indicate the direction the focus ring (29) is to be turned for focus and defocus.

I claim:

1. A microbeam holder for focusing and controlling a laser beam to a target comprising:

an annular housing with a means for attachment to a microscope;

a slip ring attached by a slip ring support retained in a support aperture defined in the annular housing;

a mirror mount having a specular mirror and an angled rod with the mirror mount mounted in the slip ring such that it rotates freely;

a joystick mechanism with a joystick retainer and a retaining ring wherein the joystick mechanism receives a ball of the angled rod;

a laser holder attached to the annular housing opposite the slip ring by means of a threaded laser holder ring attached to a laser holder retainer which laser holder retainer is mounted to the annular housing in a mounting aperture contained therein wherein the laser holder comprising:

a positive lens mount with a positive lens retained in a positive lens aperture defined therein by a positive lens retaining ring;

a negative lens mount with a negative lens retained opposite the positive lens by a negative lens retaining groove and a negative lens retainer;

a negative lens mount retaining ring with a retaining ring thread on its outside circumference mounted axially around the positive lens mount and attached to the negative lens mount by a screw which passes through the positive lens mount by a slotted aperture defined therein;

a focus ring around the positive lens mount and the negative lens mount retaining ring with a focus thread on the focus ring inside circumference to interact with the retaining ring thread wherein when the focus ring is rotated the negative lens mount retaining ring moves axially relative to the positive lens mount;

a laser mount attached to the positive lens mount at a laser mount end;

a washer and lens wave washer ring at the positive lens end and a washer at the laser mount end to stop the axially motion of the negative lens mount when moved by the focus ring;

a spot size retaining ring with a retaining screw that may be tightened against the laser mount to hold the spot size retaining ring to limit the rotational movement of the focus ring to the length of a turn groove defined in the focus ring.

2. The microbeam holder as in claim 1 wherein the means for attachment to a microscope is a protrusion on the annular housing inner circumference approximately one-quarter the length of the annular housing inner circumference and opposite a key wherein the protrusion and the key hold an attachment ring by means of an annular groove around the attachment ring outside perimeter allowing the annular housing to rotate about a lens attached to a microscope wherein the lens is retained in the attachment ring by a lens ring retainer.

3. The microbeam holder as in claim 1 wherein the ball fits into a joystick ball having a joystick handle attached and the joystick ball has a cylindrical aperture defined therein with sufficient diameter to receive the ball and has a spring in the cylindrical aperture to apply pressure on the ball and the joystick ball being held in the annular housing in a joystick aperture defined therein by the joystick retainer where the joystick retainer has the retaining ring and a retaining ring washer spring to provide tension control on the joystick ball when the threaded joystick retainer is rotated and the joystick aperture having an O-ring on the opposite side of the joystick ball from the retaining ring.

4. The microbeam holder as in claim 1 wherein a hand rest ring having a hand rest aperture around a joystick housing wherein the hand rest aperture is threaded to accept a hand rest lock compatibly threaded such that when a hand rest knurl and a hand rest attached to the hand rest lock are twisted the hand rest ring can be rotated about the joystick housing or held firmly in place by the friction of the hand rest lock such that a person's hand may rest on the hand rest.

* * * * *